United States Patent [19]

Nardi et al.

[11] 4,221,803

[45] Sep. 9, 1980

[54] SUBSTITUTED DIBENZYL ETHERS AND PHARMACEUTICAL COMPOSITIONS CONTAINING SAID ETHERS FOR THE TREATMENT OF INFECTIONS

[75] Inventors: Dante Nardi; Elena Massarani; Alberto Tajana, all of Milan; Mario Veronese, Bresso, all of Italy

[73] Assignee: Recordati, S.A., Chiasso, Switzerland

[21] Appl. No.: 37,370

[22] Filed: May 9, 1979

[51] Int. Cl.$^2$ ................ A61K 31/415; C07D 233/60
[52] U.S. Cl. ................... 424/273 R; 548/341
[58] Field of Search ................... 548/341; 424/273 R

[56] References Cited

U.S. PATENT DOCUMENTS

| | | | |
|---|---|---|---|
| 3,717,655 | 2/1973 | Godefroi et al. | 548/341 |
| 4,036,973 | 7/1977 | Walker et al. | 548/341 |

Primary Examiner—Henry R. Jiles
Assistant Examiner—Richard A. Schwartz
Attorney, Agent, or Firm—Stevens, Davis, Miller & Mosher

[57] ABSTRACT

There are provided 2,4-dichloro-4'-phenyl-α-(N-imidazolyl-methyl)-dibenzyl ether, 2,4-dichloro-4'-phenylthio-α-(N-imidazolyl-methyl)-dibenzyl ether and pharmaceutically acceptable acid addition salts thereof. These compounds show activity against some fungi, yeasts and gram positive aerobic and anaerobic bacteria. The new compounds can be prepared by condensing 1-(2',4'-dichlorophenyl)-2-(N-imidazolyl)-ethanol with 4-chloromethyl-biphenyl, 4-bromomethyl-biphenyl, 1-phenylthio-4-chloromethyl-benzene or 1-phenylthio-4-bromomethyl-benzene in a solvent, most preferably dimethylsulphoxide.

8 Claims, No Drawings

SUBSTITUTED DIBENZYL ETHERS AND PHARMACEUTICAL COMPOSITIONS CONTAINING SAID ETHERS FOR THE TREATMENT OF INFECTIONS

DESCRIPTION

The invention relates to substituted dibenzyl ethers, to methods for their preparation and to pharmaceutical compositions containing them.

The invention provides compounds of the general formula I

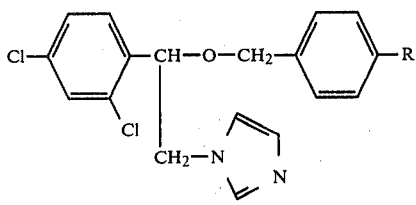

wherein R represents a phenyl or phenylthio group, that is 2,4-dichloro-4'-phenyl-α-(N-imidazolyl-methyl)-dibenzyl ether and 2,4-dichloro-4'-phenylthio-α-(N-imidazolyl-methyl)-dibenzyl ether, and pharmaceutically acceptable acid addition salts thereof.

Preferred pharmaceutically acceptable acid addition salts of the compounds I include those formed from both mineral and organic acids, such as hydrochloric, nitric, sulphuric, phosphoric, methane-sulphonic, succinic, maleic, fumaric, citric and tartaric acids. These salts may be prepared by conventional methods, for example by adding to the base in equimolecular amount the desired acid and then crystallizing the salt so obtained from a suitable solvent.

The compounds I and their salts are of interest for the activity they show against some fungi, yeasts and gram positive aerobic and anaerobic bacteria. The activity is coupled with a low toxicity. The compounds of the invention have been compared with two well-known antimycotic products, clotrimazole, i.e., [(imidazol-1-yl)-2-(o-chlorophenyl)-2,2-diphenylmethane], and miconazole.

Particularly interesting was the comparison between the activity and toxicity of the compounds I and of miconazole, which is 2,2',4,4'-tetrachloro-α-(N-imidazolyl-methyl)-dibenzyl ether. In miconazole both benzyl groups are substituted in the 2- and 4-positions by chlorine atoms, whereas in the compounds I the benzyl group which is α-unsubstituted is substituted in the 4-position by a phenyl or phenylthio group. This difference involves a notable reduction of toxicity which, for the new products, is from 3 to 4 times lower than that of miconazole, whereas the antifungal and antibacterial activity is about the same. The compounds according to the invention can be conveniently employed in human therapy for the local treatment of dermatosis, such as trichophytosis and candidosis, and further infections caused by fungi staphylococci and streptococci. The compounds according to the invention may be admixed with pharmaceutically acceptable diluents or carriers to form pharmaceutical compositions, which may be in any suitable form, for example powders, ointments, creams, suspensions and dispersions.

The results obtained in biological assays are reported in Tables I, II and III.

In Table I are reported the acute toxicity values ($LD_{50}$) of the compounds I and of both the comparison substances. Toxicity, given in mg/Kg, has been evaluated per os in the mouse by conventional methods.

In Table II are reported the minimal inhibent concentrations (MIC) of the compounds I and of both the comparison substances. For MIC, the minimal concentration is intended, i.e., one which is able to inhibit the growth of several fungi and yeasts. The MIC values have been determined according to the usual two-fold serial broth dilution technique.

The MIC values of the products under examination and of both comparison substances, referred to a certain number of gram positive bacteria and determined according to the conventional two-fold serial broth dilution technique, are reported in Table III.

Experimental conditions were as follows

For Fungi

Medium: Sabouraud liquid pH 5.7 (5 ml per tube)

Inoculum: A ten days agar culture was washed with a physiological solution containing 10% Tween 80, then filtered through gauze and again suspended in physiological solution until the solution showed on a Coleman Jr II spectrophotometer, at a wavelength of 650 nm, a 50% transparence (T) (0.1 ml of spore suspension per ml). For Aspergillus niger, after filtration, a 1/10 dilution in physiological solution was prepared. 0.1 ml of this dilution constituted the inoculum for 5 ml.

Temperature and incubation time: 25° C. for 7 days.

For Yeasts

Medium: Sabouraud liquid pH 5.7 (5 ml per tube)

Inoculum: Yeasts were grown in Sabouraud liquid for 24 hours (Cryptococcus neoformans for 2 days). Cells were collected by centrifugation at 6500 rpm and again suspended in physiological solution so as to have a suspension giving on a Coleman Jr II spectrophotometer, at a wavelength of 650 nm, a 50% transparence (T). 0.1 ml of this suspension constituted the inoculum for 5 ml.

Temperature and incubation time: 37° C. for 48 hours.

For Gram Positive Bacteria

Medium: Tryptic soy broth pH 7.3 (5 ml per tube)

Inoculum: The day before the test, the microorganisms to be tested were transplanted in their respective media. After 18 hours incubation at 37° C., 0.1 ml of a 1:100 diluted suspension of each strain in broth, were inoculated in 5 ml of medium containing the products under examination at a serial concentration of from 0.009 to 160 mcg/ml.

Temperature and incubation time: 37° C. for 18 hours.

TABLE I

| Acute toxicity ($LD_{50}$) per OS in the mouse in mg/Kg. | | | |
|---|---|---|---|
| Formula I I: R = $C_6H_5$ | Formula I I: R = $C_6H_5S$ | Miconazole | Clotrimazole |
| 2400 | 3000 | 870 | 880 |

TABLE II

| | Antimycotic activity (MIC) in mcg/ml | | | |
|---|---|---|---|---|
| Phatogenous Agent | Formula I R=C$_6$H$_5$ | Formula I R=C$_6$H$_5$S | Micanazole | Clotrimazole |
| C.Albicans R | 5 | 40 | 5 | 10 |
| C.Albicans Grunenthal | 5 | 40 | 5 | 10 |
| C.Albicans 1040 | 10 | 80 | 20 | 40 |
| C.Albicans 1041 | 20 | 80 | 20 | 40 |
| C.Neoformans | 0.312 | 0.156 | 0.078 | 0.625 |
| T.Mentagroph. 2538 | 0.156 | 0.156 | 0.078 | 0.078 |
| T.Mentagroph. 10148 | 0.625 | 0.625 | 0.625 | 1.25 |
| T.Mentagroph. 5865 | 1.25 | 1.25 | 0.31 | 0.62 |
| T.Verrucosum | 10 | 1.25 | 2.5 | 2.5 |
| T.Rubrum 2121 | 0.625 | 0.625 | 0.312 | 1.25 |
| M.Canis 28 | 20 | 2.5 | 5 | 2.5 |
| A.Niger | 20 | 10 | 40 | 10 |
| P.Chrysogenum | 20 | 5 | 20 | 40 |
| E.Floccosum | 10 | 5 | 5 | 5 |

TABLE III

| | Antibacterial activity (MIC) in mcg/ml | | | |
|---|---|---|---|---|
| Phatogenous Agent | Formula I R = C$_6$H$_5$ | Formula I R = C$_6$H$_5$S | Micanazole | Clotrimazole |
| S.aureus SG 511 | 0.039 | 0.039 | 0.312 | 0.312 |
| S.aureus 10B | 0.039 | 0.018 | 0.312 | 1.25 |
| Str.hemolyt 821 | 0.156 | 0.156 | 1.25 | 2.5 |
| B.subtilis | 0.156 | 0.078 | 0.625 | 2.5 |
| Cl. novyi | <1.25 | 5.0 | <1.25 | >160 |
| Str.hemolyt 203 | 0.312 | 0.078 | 0.625 | 5 |

The invention further provides a method for the preparation of compounds of the general formula I as hereinbefore defined, the method comprising condensing in a solvent 1-(2',4'-dichlorophenyl)-2-(N-imidazolyl)-ethanol with a halobenzyl compound of the general formula II

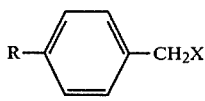

II wherein R has the meaning previously ascribed to it and X represents a chlorine or bromine atom.

As solvent, an aromatic hydrocarbon such as dimethylformamide, tetrahydrofuran, hexamethylphosphoramide and/or a mixture thereof can be employed, but it has been verified that condensation is more complete if dimethylsulphoxide is used. This leads to a higher yield and to a purer product. In this case it is not necessary to submit the base obtained from condensation to a purification through chromatographic column, whereas said purification is necessary when using as solvents dimethylformamide or hexamethylphosphoramide. A simple filtration of the base solution through a silica gel column is in fact able to retain the small amounts of impurities. For the compound I, in which R represents a phenyl group, not even the filtration is necessary, and crystallization of the nitrate leads to a product sufficiently pure for pharmaceutical purposes. With the aprotic solvents specified above, there is usually used an alkali metal hydride or amide, which is able to salify the hydroxy group of the ethanol derivative.

Alternatively the condensation solvent may be an aliphatic alcohol having from 3 to 6 carbon atoms, such as t-butanol, and in this case the alkali metal hydride or amide should be replaced by an alkali metal alcoholate, for example potassium t-butylate.

A further very useful expedient is to add small amounts of potassium iodide as catalyst before adding the halobenzyl derivative.

The 1-(2',4'-dichlorophenyl)-2-(N-imidazolyl)-ethanol may be prepared from 1-chloroacetyl-2,4-dichloro-benzene (Beilstein-Handbuch der Org. Chem. IV° ed.vol. 7, page 28) by reduction of the keto group using sodium borohydride and condensation with imidazole. The reduction and condensation can be effected in either order. The reduction may be effected in methanol and the condensation may be effected in dimethylformamide and methanol in the presence of sodium. The halobenzyl compounds of the general formula II are known. The preparation of 4-chloro-methyl-biphenyl is described in Chem. Ber. 66B, 1471, 1933 and the preparation of 1-bromomethyl-4-phenylthio-benzene is described in U.S. Pat. No. 3,242,193.

Examples 1 to 4, which follow, illustrate the invention while Examples A and B describe the preparation of the starting materials used in Examples 1 to 4.

EXAMPLE A 1-(2',4'-dichlorophenyl)-2-chloro-ethanol 49.5 g of sodium borohydride were added slowly and in small parts to a suspension of 233 g of 1-(1'-hydroxy-2'-chloroethyl)-2,4-dichloro-benzene in 1 liter of methanol stirred at room temperature. The solution thus obtained was stirred at room temperature for a further two hours, and it was then poured into 1 liter of 5 N hydrochloric acid cooled with ice. After extraction with ethyl acetate or chloroform, the extract was washed with water, with 1 N sodium hydroxide, then again with water until neutrality, and finally with a saturated sodium chloride solution. The extract was dried, the solvent evaporated off and 220 g of an oil were obtained. The oil solidified on standing and the solid melted at 48°–51° C.

| Analysis for C$_8$H$_7$Cl$_3$O | C% | H% | Cl% |
|---|---|---|---|
| Calculated | 42.61 | 3.13 | 47.17 |
| Found | 42.75 | 3.19 | 47.43 |

EXAMPLE B 1-(2',4'-dichlorophenyl)-2-(N-imidazolyl)-ethanol 30 g of sodium were added to a solution of 88.5 g of imidazole in 600 ml of methanol; the solvent was then evaporated off. The residue was dissolved in 300 ml of dimethylformamide and heated to 115°–120° C. To the solution so obtained was added, dropwise and under stirring, a solution of 225 g of 1-(2',4'-dichlorophenyl)-2-chloro-ethanol in 400 ml of dimethylformamide. The mixture was heated to 115°–120° C. and maintained at that temperature for 20 minutes and, after subsequent cooling to 40° C., 2500 ml of iced water were added under vigorous stirring. The product precipitated under stirring over a period of about two hours, the upper liquid was then decanted off, a further 2500 ml of water were added and, after standing, the whole was filtered. The precipitate thus obtained was dried and crystallized from toluene. 170 g of the desired product, melting at 134°–135° C., was obtained.

| Analysis for C$_{11}$H$_{10}$Cl$_2$N$_2$O | C% | H% | N% | Cl% |
|---|---|---|---|---|
| Calculated | 51.38 | 3.92 | 10.89 | 27.58 |

| Analysis for $C_{11}H_{10}Cl_2N_2O$ | C% | H% | N% | Cl% |
|---|---|---|---|---|
| Found | 51.62 | 3.80 | 10.73 | 27.76 |

EXAMPLE 1

2,4-Dichloro-4'-phenylthio-α-(N-imidazolyl-methyl)-dibenzyl ether (I: R=$C_6H_5S$)

METHOD I

A solution of 2.57 g of 1-(2',4'-dichlorophenyl)-2-(N-imidazolyl)-ethanol, prepared as described in Example B, in 10 ml of hexamethylphosphoramide was dropped at 25° C. into a suspension of 0.52 g of sodium hydride (50% in oil) in 5 ml of hexamethylphosphoramide. When hydrogen emission was over, the salification was completed by heating for 1 hour at 50° C. After cooling to 25° C., 2.58 g of 1-chloromethyl-4-phenylthio-benzene were added. The temperature was raised to 50° C. and maintained at that temperature for 12 hours. At the end of the reaction, the mixture was poured into 200 ml of water, the product was extracted with diethyl ether, the solvent was evaporated off and the residue was purified twice on a silica gel column, using ethyl acetate as eluant and testing the various fractions by TLC. The solvent was evaporated off the middle fractions to give 2.4 g of the desired base as a yellowish oil, showing a single spot on TLC.

| Analysis for $C_{24}H_{20}N_2Cl_2OS$ | C% | H% | N% | Cl% | S% |
|---|---|---|---|---|---|
| Calculated | 63.30 | 4.44 | 6.13 | 15.57 | 7.04 |
| Found | 63.86 | 4.24 | 6.41 | 15.29 | 6.97 |

METHOD II 0.66 g of sodium hydride (50% in oil) were added at 20°-30° C. and under nitrogen atmosphere to 3.86 g of 1-(2',4'-dichlorophenyl)-2-(N-imidazolyl)-ethanol in 15 ml of dimethylsulphoxide (dried on calcium hydride).

The mixture was heated under stirring at 50°-60° C. until gas emission was over. After cooling to 20°-25° C., 0.5 g of potassium iodide were added and slowly a solution of 3.51 g of 1-chloromethyl-4-phenylthio-benzene in 4 ml of dimethylsulphoxide was dropped in. The mixture was stirred at 20°-25° C. until addition of the 1-chloro-methyl-4-phenylthio-benzene was over. The mixture was then poured into 150 ml of water and extracted with diethyl ether. To the etheric solution, after drying on anhydrous sodium sulphate, was added excess 4 N nitric acid solution in diethyl ether: the desired product precipitated as nitrate, an oil which solidified on standing. After standing for 20 hours, the etheric liquid was decanted off and the residue was crystallized from ethanol. The nitrate thus obtained, not completely pure, was dissolved in water and excess sodium carbonate was added in order to liberate the base which was then extracted with ethyl acetate. The base, obtained by filtration, was purified on a silica gel column using ethyl acetate as eluant. The combined fractions containing the desired product were evaporated to dryness. The residue was dissolved in diethyl ether, again transformed into the nitrate and crystallized from ethanol. Yield: 3.1 g of a white crystalline powder, melting at 134° C.

| Analysis for $C_{24}H_{20}N_2Cl_2O S . HNO_3$ | C% | H% | N% | Cl% | S% |
|---|---|---|---|---|---|
| Calculated | 55.61 | 4.08 | 8.11 | 13.68 | 6.18 |
| Found | 55.32 | 4.08 | 8.16 | 13.56 | 6.32 |

EXAMPLE 2

2,4-Dichloro-4'-phenyl-α-(N-imidazolyl-methyl)-dibenzyl ether (I: R=$C_6H_5$)

METHOD I

A mixture consisting of 2.02 g of potassium t-butylate in 30 ml of t-butanol was prepared at 20°-25° C. and in nitrogen atmosphere. 3.86 g of 1-(2',4'-dichlorophenyl)-2-(N-imidazolyl)-ethanol, prepared according to Example B, were added. The solution was refluxed for 1 hour and then cooled to 20°-25° C. 3.03 g of 4-chloromethyl-biphenyl were added, and the solution was again refluxed for 5 hours. After cooling to 20°-25° C. the whole was poured into water and the base extracted with ethyl acetate. The extract was washed with diethyl ether and the solvent evaporated off. The residue was dissolved in diethyl ether (80 ml) and left to stand overnight. The insoluble substances were filtered off and the filtrate was treated with nitric acid dissolved in diethyl ether. An oil, which solidified on standing, was obtained. The residue, consisting of 2,4-dichloro-4'-phenyl-α-(N-imidazolyl-methyl)-dibenzyl ether nitrate, was crystallized from ethanol or ethyl acetate. A product (4.3 g), shown to be pure on TLC and melting 140°-141° C., was obtained.

| Analysis for $C_{24}H_{20}N_2Cl_2O . HNO_3$ | C% | H% | N% | Cl% |
|---|---|---|---|---|
| Calculated | 59.25 | 4.35 | 8.64 | 14.57 |
| Found | 59.17 | 4.14 | 8.61 | 14.46 |

METHOD I(a)

To a solution of 0.37 g of sodium metal in 20 ml of n-propanol, 4.1 g of 1-(2',4'-dichlorophenyl)-2-(N-imidazolyl)-ethanol were added and the mixture was refluxed for two hours under stirring. After cooling to room temperature, 0.5 g of potassium iodide and 3.25 g of 4-chloromethyl-biphenyl were added under stirring and the mixture was again refluxed. At the end of the reaction, the mixture was filtered off and washed with ethanol. The filtrate was evaporated to dryness and the residue dissolved in diethyl ether. The insoluble residue was filtered off and the clear etheric solution thus obtained was treated with a mixture of nitric acid and diethyl ether. The 2,4-dichloro-4'-phenyl-α-(N-imidazolyl-methyl)-dibenzyl ether nitrate so formed was crystallized from ethanol. A product (2.1 g) having the same characteristics as that prepared according to the previous method and showing a single spot on TLC was obtained.

METHOD II 0.66 g of sodium hydride were added, under nitrogen atmosphere and at 20°-25° C., to a solution of 3.86 g of 1-(2',4'-dichlorophenyl)-2-(N-imidazolyl)-ethanol in 15 ml of dimethylsulphoxide (dried on calcium hydride). The mixture was heated at 50°-60° C. until gas emission was over. The mixture was then cooled to 20°–25° C., 0.5 g of potassium iodide were added and a solution of 3.03 g of 4-chloromethyl-biphenyl in 7 ml of dimethylsulphoxide (dried on calcium hydride) was dropped in. The whole was stirred for about 20 hours at 20°–25° C. and then poured into water. The product was extracted with ethyl acetate and then treated as described in Method I. Yield 4.6 g.

EXAMPLE 3

Salts of 2,4-dichloro-4'-phenylthio-α-(N-imidazolyl-methyl)-dibenzyl ether were prepared by reacting the free base, dissolved in ethanol, with an alcohol solution of the desired acid and subsequently crystallizing the salt so obtained from a suitable solvent. The free base was prepared according to Example 1, Method I, or by liberation from its nitrate, prepared according to Method II, by treatment with sodium carbonate, extraction with diethyl ether and evaporation.

In Table IV the solvents of crystallization, the elemental analysis and the melting points of some salts are reported.

In Table V are listed the same data for some salts of 2,4-dichloro-4'-phenyl-α-(N-imidazolyl-methyl)-dibenzyl ether, obtained using the methods described above.

| Ointment | |
|---|---|
| 2,4-dichloro-4'-phenylthio-α-(N-imidazolyl-methyl)-dibenzyl ether nitrate | 2 g |
| Lanolin | 20 g |
| Vaseline q.s. to | 100 g |
| Glycolic solution | |
| 2,4-dichloro-4'-phenylthio-α-(N-imidazolyl-methyl)-dibenzyl ether nitrate | 2 g |
| Propylene Glycol q.s. to | 100 ml |
| Powder | |
| 2,4-dichloro-4'-phenylthio-α-(N-imidazolyl-methyl)-dibenzyl ether nitrate | 2 g |
| Lanolin | 1.5 g |
| Soybean lecithin | 2 g |
| Talc q.s. to | 100 g |
| Gel | |
| 2,4-dichloro-4'-phenylthio-α-(N-imidazolyl-methyl)-dibenzyl ether nitrate | 2 g |
| Carbopol | 2 g |
| Water | 2 g |
| Polyethylene glycol q.s. to | 100 g |
| Triethanolamine q.s. to about pH 3 | |

What is claimed is:

1. 2,4-Dichloro-4'-phenylthio-α-(N-imidazolyl-methyl)-dibenzyl ether or a pharmaceutically acceptable acid addition salt thereof.

2. 2,4-Dichloro-4'-phenyl-α-(N-imidazolyl-methyl)-dibenzyl ether or a pharmaceutically acceptable acid addition salt thereof.

3. The ether of claim 1 in the form of an acid addition

TABLE IV

| Salt | Solvent of crystallization | M.P. | Calculated | | | | | Found | | | | |
|---|---|---|---|---|---|---|---|---|---|---|---|---|
| | | | C% | H% | N% | Cl% | S% | C% | H% | N% | Cl% | S% |
| Hydrochloride | Isopropanol | 181–183° C. | 58.61 | 4.30 | 5.69 | 21.62 | 6.51 | 58.42 | 4.31 | 5.67 | 21.40 | 6.79 |
| Maleate | Ethanol | 117–118° C. | 58.85 | 4.23 | 4.90 | 12.41 | 5.61 | 58.61 | 4.50 | 4.77 | 12.24 | 5.91 |
| Methanesulphonate | Ethanol | 153–155° C. | 54.45 | 4.39 | 5.08 | 12.86 | 11.63 | 54.21 | 4.32 | 4.78 | 12.97 | 11.94 |
| p-toluene-sulphonate | Ethanol | 127–128° C. | 59.33 | 4.50 | 4.46 | 11.30 | 10.22 | 59.43 | 4.49 | 4.43 | 11.63 | 10.44 |
| Phosphate | Ethanol | 143–145° C. | 52.09 | 4.19 | 5.06 | 12.81 | 5.79 | 51.86 | 4.18 | 5.12 | 12.90 | 5.91 |

TABLE V

| Salt | Solvent of crystallization | M.P. | Calculated | | | | | Found | | | | |
|---|---|---|---|---|---|---|---|---|---|---|---|---|
| | | | C% | H% | N% | Cl% | S% | C% | H% | N% | Cl% | S% |
| Hydrochloride | Ethyl Acetate | 171–172° C. | 62.69 | 4.60 | 6.09 | 23.13 | | 62.40 | 4.80 | 5.86 | 23.18 | |
| Sulphate | Ethanol | 72–80° C. | 55.28 | 4.25 | 5.37 | 13.60 | 6.15 | 54.99 | 3.90 | 5.25 | 13.48 | 6.23 |
| Maleate | Ethanol | 128–129° C. | 62.35 | 4.48 | 5.19 | 13.14 | | 62.05 | 4.19 | 4.91 | 13.51 | |
| p-toluene-sulphonate | Ethanol | 182–184° C. | 64.25 | 4.87 | 4.83 | 12.23 | 5.53 | 63.81 | 4.82 | 4.54 | 12.52 | 5.63 |
| Citrate | Ethanol | 150° C. | 58.55 | 4.58 | 4.55 | 11.52 | | 58.97 | 4.47 | 4.61 | 11.60 | |

EXAMPLE 4

Pharmaceutical antifungal and antibacterial formulations, comprising active compounds according to the invention at concentrations of from 0.5 to 5% by weight, preferably from 1 to 3% by weight, in admixture with pharmaceutically acceptable diluents or carriers, were prepared. Examples of the composition of an ointment, a powder, a glycolic solution and a gel are given below.

salt selected from the group consisting of hydrochloride, nitrate, maleate, methanesulphonate, p-toluenesulphonate and phosphate.

4. The ether of claim 2 in the form of an acid addition salt selected from the group consisting of hydrochloride, nitrate, sulphate, a maleate, p-toluenesulphonate and citrate.

5. A pharmaceutical composition for the treatment of infections caused by fungi, yeasts and gram positive aerobic and anaerobic bacteria comprising an effective amount of a compound of the formula

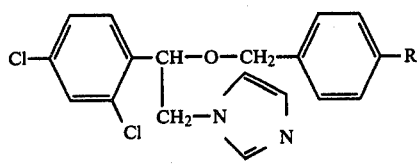

wherein R represents a phenyl or phenylthio group, or a pharmaceutically acceptable addition salt thereof, in admixture with a pharmaceutically acceptable diluent or carrier.

6. The pharmaceutical composition according to claim 5 in which the compound is present in an amount of from 0.5 to 5% by weight.

7. The pharmaceutical composition according to claim 5 in which the compound is present in an amount of from 0.5 to 3% by weight.

8. The pharmaceutical composition according to claim 5, 6 or 7 in the form of an ointment, a powder, a glycolic solution or a gel.

* * * * *